US007618450B2

(12) United States Patent
Zarowski et al.

(10) Patent No.: US 7,618,450 B2

(45) Date of Patent: Nov. 17, 2009

(54) IMPLANTABLE HEARING SYSTEM

(75) Inventors: Andrzej Zarowski, Wilrijk (BE); Nick Van Ruiten, 'S Gravenwezel (BE)

(73) Assignee: 3WIN N.V., Niel (BE)

( * ) Notice: Subject to any disclaimer, the term of this patent is extended or adjusted under 35 U.S.C. 154(b) by 563 days.

(21) Appl. No.: 10/541,226

(22) PCT Filed: Dec. 30, 2003

(86) PCT No.: PCT/EP03/14982

§ 371 (c)(1),
(2), (4) Date: Feb. 13, 2006

(87) PCT Pub. No.: WO2004/060015

PCT Pub. Date: Jul. 15, 2004

(65) Prior Publication Data

US 2006/0161255 A1 Jul. 20, 2006

(30) Foreign Application Priority Data

Dec. 30, 2002 (EP) .................................. 02080679

(51) Int. Cl.
*A61F 2/18* (2006.01)
*H04R 25/00* (2006.01)

(52) U.S. Cl. ........................................... 623/10; 600/25

(58) Field of Classification Search ................... 623/10; 600/22–25; 381/68–69.2
See application file for complete search history.

(56) References Cited

U.S. PATENT DOCUMENTS

| | | | | |
|---|---|---|---|---|
| 5,531,787 | A | 7/1996 | Lesinski | |
| 5,772,575 | A | 6/1998 | Lesinski | |
| 5,984,859 | A * | 11/1999 | Lesinski | 600/25 |
| 6,005,955 | A | 12/1999 | Kroll | |
| 6,068,589 | A * | 5/2000 | Neukermans | 600/25 |
| 6,381,336 | B1 * | 4/2002 | Lesinski et al. | 381/326 |
| 6,629,923 | B2 * | 10/2003 | Leysieffer | 600/25 |
| 6,648,914 | B2 * | 11/2003 | Berrang et al. | 623/10 |
| 7,250,059 | B2 * | 7/2007 | Reitan et al. | 623/10 |
| 2002/0035309 | A1 | 3/2002 | Leysieffer | |
| 2005/0020873 | A1 * | 1/2005 | Berrang et al. | 600/25 |

FOREIGN PATENT DOCUMENTS

FR 2 688 132 9/1993

* cited by examiner

*Primary Examiner*—Suzette J Gherbi
(74) *Attorney, Agent, or Firm*—Jacobson Holman PLLC

(57) ABSTRACT

A combined set (71) comprising a vibration actuator and an implantable device to be used as an artificial fenestrum implantable in a bony wall (25) of an inner ear, said device comprising a frame (32) made of a bio-compatible material and provided to be applied at least partially in said bony wall, said frame being provided with a wall part formed by a membrane (27) forming a barrier with a perilymph of said inner ear when applied in said bony wall, said membrane being provided to form together with said frame an interface with said inner ear, said interface being provided for energy transfer towards and from said inner ear, said membrane being electrically dissociated from said vibration actuator and provided for receiving vibration energy from said vibration actuator.

26 Claims, 12 Drawing Sheets

IMPLANTABLE HEARING SYSTEM

This is a 371 of PCT/EP03/014982 filed Dec. 30, 2003.

The present invention relates to a combined set comprising a vibration actuator and an implantable device to be used as an artificial enestrum implantable in a bony wall of an inner ear, said device comprising a frame made of a bio-compatible material and provided to be applied at least partially in said bony wall, said frame being provided with a wall part formed by a membrane made of a bio-compatible material and forming a barrier with a perilymph of said inner ear when applied in said bony wall, said membrane being provided to form together with said frame an interface with said inner ear, said interface being provided for energy transfer, in particular mechanical and/or electrical and/or electromagnetic energy, towards said inner ear, said vibration actuator being provided for generating a vibration energy.

Such a combined set is known from U.S. Pat. No. 5,772,575. The known set forms an implantable hearing aid provided to be implanted in a temporal bone of a human being. The known hearing aid comprises a micro-actuator, which includes a disk-shaped transducer, which is attached to an end of a tube forming the frame of the implantable device. The tube comprises external threads enabling the tube to be screwed into a fenestration formed through the promontory of the middle ear cavity. The transducer is fabricated from a thin circular disk of piezoelectric material. The transducer comprises two electrodes situated at opposite sides of the piezoelectric element. Application of a potential difference across the electrodes causes the disk to become either more or less bowed, depending upon the polarity of the applied voltage. The transducer is soldered to one end of the tube, in such a manner that it faces the perilymph fluid of the cochlea. Since the transducer comprises electrodes on both sides, the electrodes face the perilymph fluid. The transducer deflects when a voltage is applied across the electrodes thereby generating fluid vibrations within the perilymph fluid at the frequency of the applied voltage. Preferably, a very thin metallic diaphragm, having a rim is hermetically sealed on the end of the tube. The disk-shaped transducer is contained entirely within the tube and is conductively attached to the diaphragm with a conductive cermet layer juxtaposed with the diaphragm. The diaphragm serves as a support for the disk-shaped transducer and deforms in conformity with the transducer.

Modification and/or amplification of the energy reaching the sensory cells of the inner ear are the basis for treatment of conductive and sensorineural hearing losses. First attempts to improve hearing by making a hole in the wall of the inner ear at the level of the lateral semicircular canal have been undertaken already in 1914 by Jenkins and improved by Lempert in 1938. This procedure, called “fenestration” (where a trough-shaped window made in the bony wall of the inner ear was covered with transposed tympanic membrane) attempted to connect the fluid spaces of the human inner ear directly to the outside world bypassing the dysfunctional middle ear. This procedure enabled the sound energy to reach directly the membranous part of the inner ear and could result in an improvement of hearing by up to 30 dB.

Currently, when opening of the inner ear space is necessary, other—safer and more effective—surgical techniques have been developed. In patients with otosclerosis (immobility of the ossicular chain due to fixation of the stapes footplate) a small-hole fenestration in the stapes footplate is made and a Teflon piston is transposed between the incus and the opening in the footplate (after removal of the stapes superstructure). This procedure, albeit quite difficult technically, allows for normalisation of the functional status of the conductive part of the middle ear and in most cases is able to restore hearing to normal or quasi-normal.

The main drawback of the latter technique is that the fenestration of the inner ear remains open, which incurs the risk for inner ear infections possibly followed by meningitis or total hearing loss, or is covered with a piece of tissue having in the long term a tendency to reossify, which leads to diminished results.

Amplification of the energy reaching the sensory cells of the inner ear could also be achieved in a variety of hearing aids. All these devices try to compensate for the diminished hearing acuity by amplification of the energy reaching the inner ear (either as the amplified sound wave in the air or as a vibration coupled to the ossicular chain or transferred through the bones of the skull). However, application of any one of these devices has important drawbacks—from cosmetic non-acceptance, feedback and distortion in classical hearing aid to limited indications and variable results in implantable hearing aids.

There have also been a few devices described in the literature, which employ a direct energy transfer to or from the inner ear. The advantage of these systems is that relatively little energy is required to achieve substantial amplifications and that the transducers can be very small.

The Round Window Electromagnetic device (RWEM) realises coupling to the cochlear fluids through an intact round window membrane, which serves here as the natural flexible interface between the middle and the inner ear. The RWEM uses a magnet surgically placed onto the round window and an electromagnetic coil to induce vibration. This vibration is transmitted through an intact round window membrane into the cochlea’s fluids. The RWEM device, however, would compromise the normal compliance of the round window membrane, which could induce a hearing loss. There is no teaching in this prior art to make use of an artificial fenestration device.

Money (U.S. Pat. No. 5,782,744) proposed an implantable microphone encapsulated in a waterproof casing and placed at the round window in contact with the cochlear fluid, immersed in the cochlear fluid or placed in the middle ear and coupled to the inner ear fluid by a conduction tube. The advantage of such microphone is that it can precisely transmit the pressure variations induced in the inner ear by acoustic stimulation. Yet there is no teaching in this prior art to make this system suitable for mechanical stimulation of the cochlear fluids.

Gilman (U.S. Pat. No. 5,176,620) proposed transmission of acoustic energy between a remote pressure generator and the inner ear via a liquid filled tube terminated with a membrane and placed at the round window. There is however no teaching in this prior art to use a separate, universal device as the hermetic interface between the middle and inner ear and allowing for connection with it of the transmission tube or other stimulating and/or sensing members.

A drawback of the known implantable combined set (U.S. Pat. No. 5,772,575) is that the tube applied on the promontory and the micro-actuator forms a whole. The piezoelectric material, its electrodes and the conductive diaphragm, which are part of the transducer, form a structural part of the tube. It is the transducer with its electrodes and with or without its diaphragm, which forms the barrier between the inner volume of the tube and the perilymph fluid. The diaphragm, which is part of the transducer, is galvanically coupled to the transducer and functions as the electric conductor between the tube and the electrodes applied on the piezoelectric material. There is no teaching in the prior art to consider this barrier as a construction part of the frame and thus to make the frame and the wall part a stand alone device capable to operate as an interface for the transfer of energy to and from the inner ear. Therefore this barrier is not galvanically insulated from the electrical signal applied on the electrodes in order to make the transducer vibrate and induce vibrations into the perilymph fluid. There is no teaching in this prior art to electrically dissociate the membrane from said vibration actuator and thus to insulate this barrier from these electric signals. The known device is only suitable for electrically generating said vibrations directly within the transducer facing the perilymph fluid.

It is an object of the present invention to realise an implantable combined set to be used as an artificial fenestrum implantable in the bony wall of the inner ear, enabling mechanical pressure as well as other manners to induce vibrations in said perilymph. Such combined set is used for energy transfer to the inner ear and is suitable for treatment of a wide range of otological pathologies.

For this purpose, an implantable combined set according to the present invention is characterised in that said membrane is electrically dissociated from said vibration actuator and provided for receiving said vibration energy from said vibration actuator, said membrane being further provided for transferring energy from said inner ear. By having the membrane electrically dissociated from the vibration actuator, which generates the vibrations, the vibrations are transferred from the actuator via the membrane into the perilymph fluid, without electrical current streaming through the membrane. It thus becomes possible to apply other signals such as mechanical or pressure signals on the perilymph fluid. This set-up enables to electrically dissociate the frame from the vibration actuator, thus allowing to connect a large variety of actuators to the device.

An implantable device as component of the combined set can be used as a stand-alone interface suitable for energy transfer between the middle and inner ear. In a normal hearing organ there exist two natural openings, also called windows, connecting the middle and the inner ear, one of them interfacing with the vibrating ossicular chain of the middle ear and the other one serving as a pressure equalizer. The implantable device, as component of the combined set, is based on a concept of creating an additional opening—"third window" between the middle and inner ear. This is meant for coupling of the physiological vibrations of the ossicular chain to the inner ear or it can work in the reverse mode, serving as the membrane of a microphone or as a sensor of electrical potentials generated in the inner ear.

A first preferred embodiment of a combined set according to the invention is characterised in that said vibration actuator comprises an electrical signal output circuitry provided for output of said vibration energy, said membrane being electrically dissociated from said circuitry. In such a manner the electrical dissociation between membrane and actuator is maintained.

A second preferred embodiment of a combined set according to the invention is characterised in that said device is provided with connecting means applied on said frame, said connecting means being provided for receiving and connecting a stimulating and/or a sensing member into said frame in such a manner as to enable said energy transfer. In such a manner, a stimulating and/or sensing member can easily be connected inside the frame.

Preferably, a mechanically driven piston is mounted into said frame, said piston being mounted in such a manner as to mechanically contact said membrane. Mechanically driven pistons provide a reliable and accurate vibration generator.

The invention also relates to an implantable device as a component of a combined set according to the invention. Preferably such an implantable device is characterised in that said membrane is provided for transferring energy to and from said inner ear.

A first preferred embodiment of a device as a component of a combined set according to the invention is characterised in that said membrane is provided to form a substantially hermetical closure between said perilymph and an inner part of said frame, when applied in said inner ear. By forming such a hermetical closure, contamination of the perilymph and the inner ear is substantially reduced.

A second preferred embodiment of a device as a component of a combined set according to the invention is characterised in that a side of said membrane, provided to contact said perilymph when said device is mounted in said inner ear, is provided with an electrically conductive layer which is connected to a conductive wire, applied in an electrically insulated manner on said frame. This enables to bring an electrode in direct contact with the perilymph fluid without affecting the electrical insulation of the membrane.

The invention will now be described in more details with reference to the annexed drawings illustrating a plurality of embodiments for a combined set having an implantable device according to the present invention. In the drawings:

FIG. 1 is a schematic coronal view through a human temporal bone illustrating the external, middle and inner ears and showing the relative positions of the implantable device as component of the combined set in accordance with the present invention;

FIGS. 2A to C show in a detailed manner how the implantable device, as component of the combined set, is implanted in the wall of the inner ear;

FIGS. 3A to F show cross-sections of different embodiments of the implantable device, as component of the combined set, of the present invention;

FIG. 4A shows a top view and FIGS. 4B to D show a side view of different embodiments of the implantable device, as component of the combined set, of the present invention;

FIGS. 5A to D show cross-sections of other embodiments of the implantable device, as component of the combined set, according to the present invention;

Figure 1:
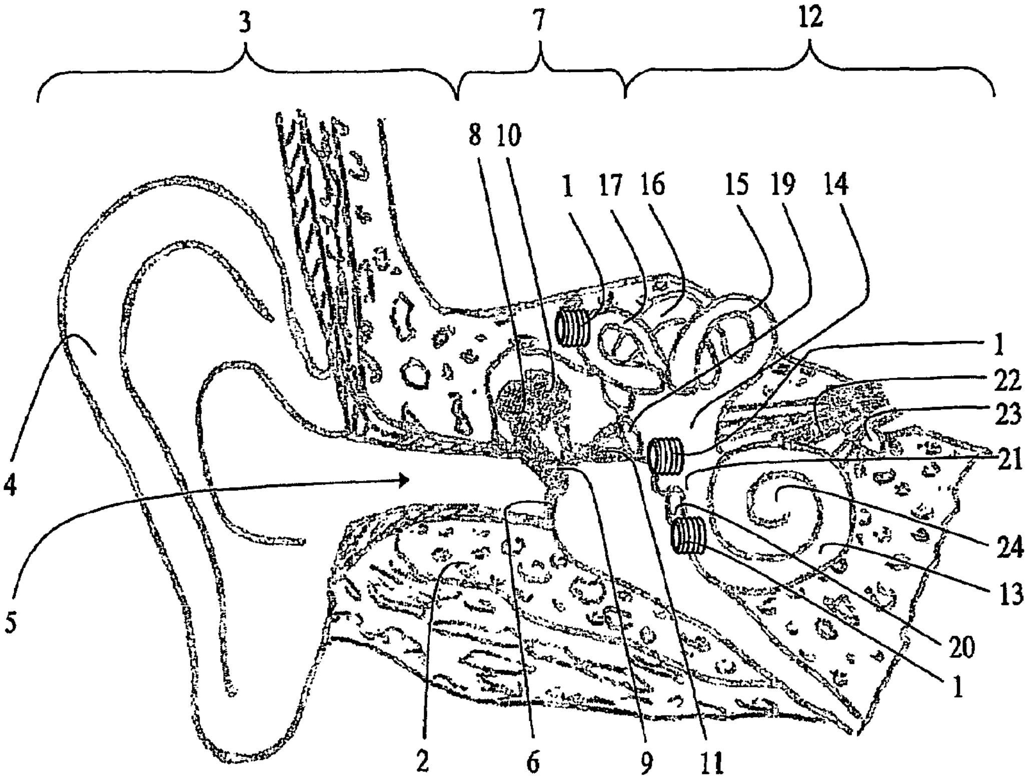

In the drawings, a same reference sign has been assigned to a same or analogous element.

FIG. 1 illustrates relative locations of components of an implantable device 1, as component of a combined set, in accordance with the present invention, after implantation in a temporal bone 2 of a human being. This figure also illustrates an external ear 3 with a pinna 4 and an external auditory canal 5. A medial end of the external auditory canal ends with an ear drum or tympanic membrane 6, which forms an interface between the external ear 3 and the middle ear 7. The tympanic membrane 6 mechanically vibrates in response to sound waves entering the external auditory canal 5.

The middle ear 7 is an air filled space comprising three ossicles, namely a hammer 8, connected with a shaft 9 to the tympanic membrane 6, an incus 10 and a stapes 11, forming together an ossicular chain. The tympanic membrane, together with the ossicular chain, is responsible for transmission of the sound pressure to an inner ear 12.

The fluid-filled inner ear 12 is comprised in an otic capsule—a dense bone forming two distinguishable parts: a snail-like cochlea 13—being a part of the hearing organ and a vestibule 14 together with an anterior 15, posterior 16 and lateral 17 semicircular canals—being the balance organ. The bony shell of the inner ear is filled with the perilymph fluid and comprises membranous structures, the so-called membranous labyrinth. The membranous labyrinth divides the perilymphatic space on the upper part, the so-called scala vestibuli, and the lower part, called the scala tympani. The membranous labyrinth is filled with the endolymph fluid and comprises the sensory cells.

The vestibule 14 communicates with the middle ear 7 through two openings, namely the oval window 19 and the round window 20. The oval window is the receptacle for the footplate of the stapes 11, which is flexibly suspended by means of an annular ligament. The round window 20 is closed and isolated from the middle ear by a thin flexible round window membrane.

Bulging of the bone over the vestibule 14 and the proximal part of the basilar cochlear turn, between the oval 19 and round windows 20, is called promontorium 21. Bundles of nerve fibres 22 (acoustic and vestibular nerves) connect the sensory cells of the inner ear 12 with the brain. These nerves, accompanied by a facial nerve, leave the temporal bone through the internal auditory canal 23 and subsequently enter appropriate nuclei in the brainstem. From these nuclei the central auditory pathways lead the signal to the auditory cortex.

The acoustic wave entering the external ear canal 5 is collected by the drum 6 and causes its vibration. This vibration is then transmitted to the inner ear 12 through the ossicular chain. The footplate of the stapes 19 is the interface between the middle 7 and the inner ear 12. The vibration of the stapes footplate results in formation of the hydrodynamic travelling wave in the fluid spaces of the inner ear 12. This wave originates at the oval window 19 and travels along the scala vestibuli towards the apex 24 of the cochlea 13 and then further down the scala tympani to the round window 20. This wave causes excitation of the sensory cells located on the basilar membrane. Displacement of the basilar membrane bends "cilia" of the receptor cells. The shearing effect of the cilia causes depolarisation and excitation of the receptor cells. Excited receptor cells generate electrical signals transmitted through the auditory nerve fibres 22 through the brainstem to the temporal lobe of a brain, where these electrical signals elicit sensations perceived as sound.

One of the three preferred localisations of the implantable device 1 into the ear, as shown in FIG. 1, is the wall of the promontorium 21, the other one is in the wall of the lateral semicircular canal 17 and the third one is at the level of the round window niche 20. The localisation in the wall of the promontorium 21 should be chosen in such a manner that the implantable device 1 enters the scala vestibuli, well above the basilar membrane. The device can also be implanted in other locations in the inner ear wall than the ones already mentioned. Such other locations (not shown in the figure) could be the bony wall of one of the other semicircular canals or, for example, the stapes footplate 19.

Figure 2A:
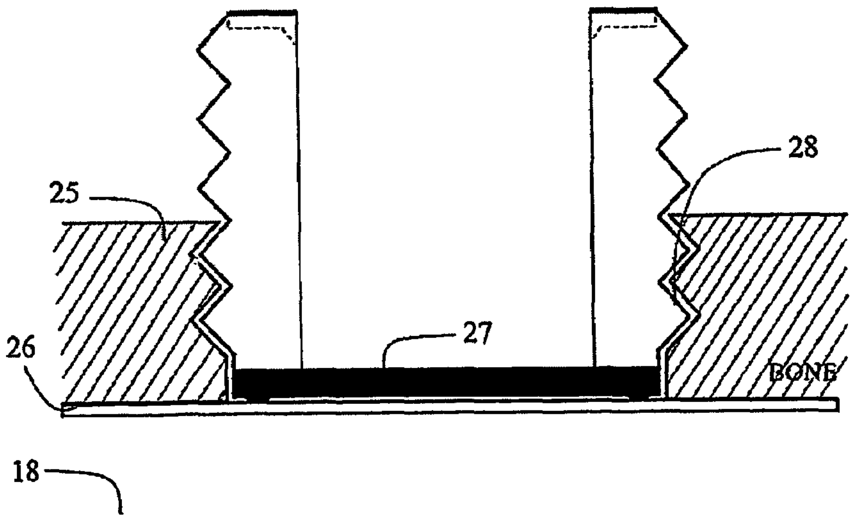
Figure 2B:
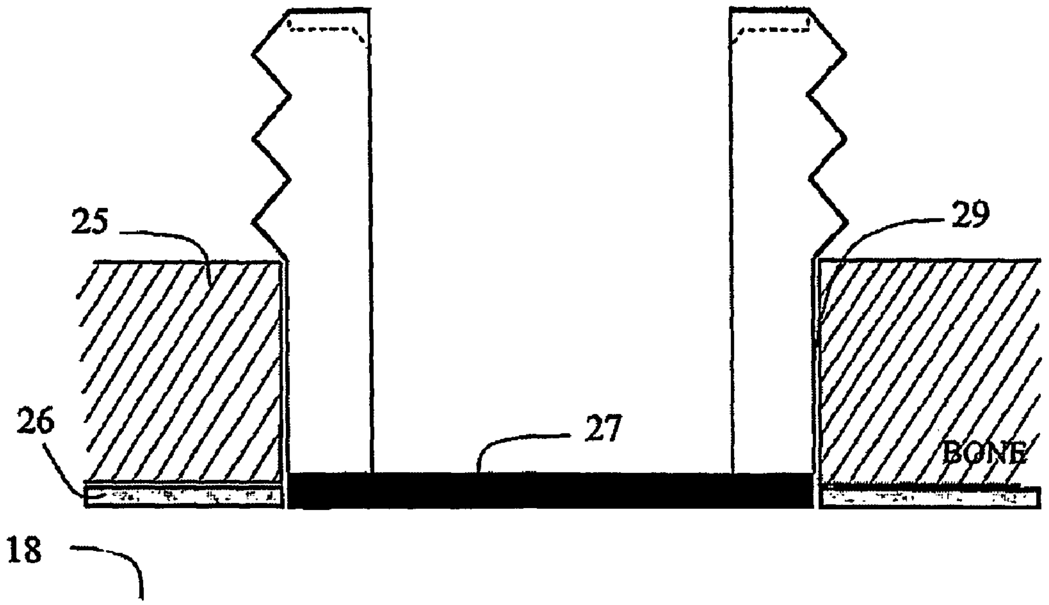
Figure 2C:
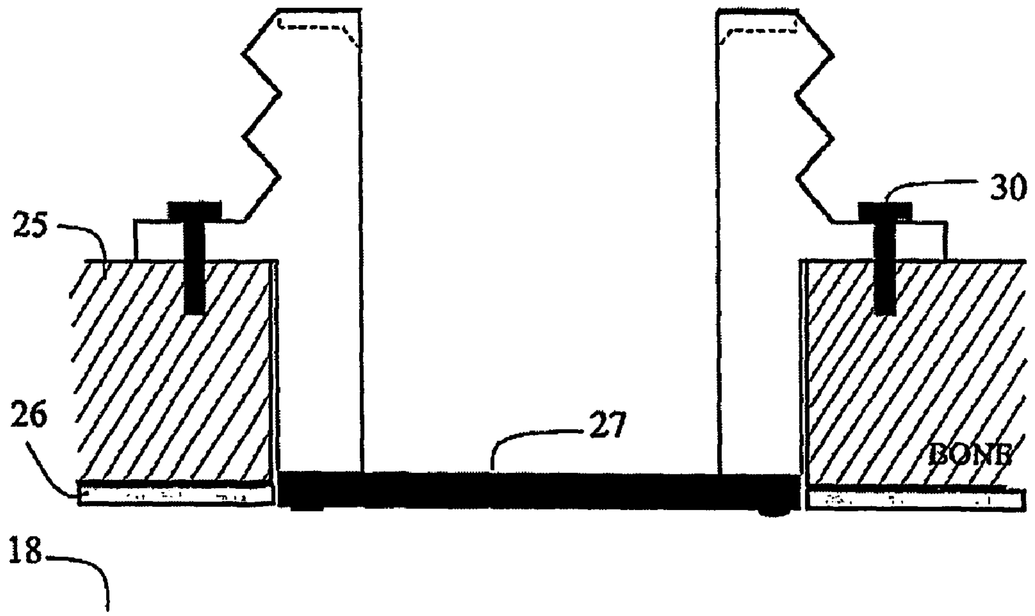

FIGS. 2A to C illustrate in detail how the device according to the invention is placed in the bony wall 25 of the inner ear 12. The preferred implantation technique applies the device 1 in such a manner that it penetrates through the bony wall of the inner ear, thereby leaving the internal endosteum 26 intact, such as illustrated in FIG. 2A. In this way the device has no direct contact with the fluid space of the perilymph 18, thereby substantially decreasing the number of potential complications. However, due to the fact that said membrane 27 of the implantable device 1 as component of the combined set hermetically isolates the inner ear fluid spaces 18 from the middle ear 7, it is also possible to implant the device 1 in such a way that it penetrates through the endosteum 26, placing the device in direct contact with the perilymph fluid 18, as illustrated in FIGS. 2B and C.

In order to apply the device in the bony wall 25, a fenestration is first drilled in this bony wall 25. The fenestration is preferably stepwise made by increasing the depth, using custom-made diamond drilling heads with increasing lengths. Such a technique reduces considerably the risk of iatrogenic complications, such loss of hearing, due to destruction of the membranous labyrinth contained within the otic capsule. After creation of the fenestration, surgical implantation of the device can be performed by screwing it into a pre-tapped opening 28 in the inner ear bony wall 25, as shown in FIG. 2A. While screwing the device into the bony wall preferably a predetermined torque is applied. The device can also be pushed into a precisely calibrated opening 29 in the inner ear wall, as shown in FIG. 2B. In this case additional external fixation of the device with micro-screws 30 or bone cement can be necessary, such as illustrated in FIG. 2C.

The device is made of a bio-compatible material such as for example titanium. The latter being particularly suitable for a direct, very strong, connection with the bone tissue, due to osseointegration.

In order to improve the fixation of the device in the bone the said frame of the device can be coated with a substance promoting bone tissue growth, e.g. hydroxyapatite.

The microbiological safety can additionally be improved by coating of said frame of the device with a substance improving hermeticity of insertion into said perilymph, e.g. silicone with swelling properties; the frame itself can also be coated with antibiotics.

Figure 3A:
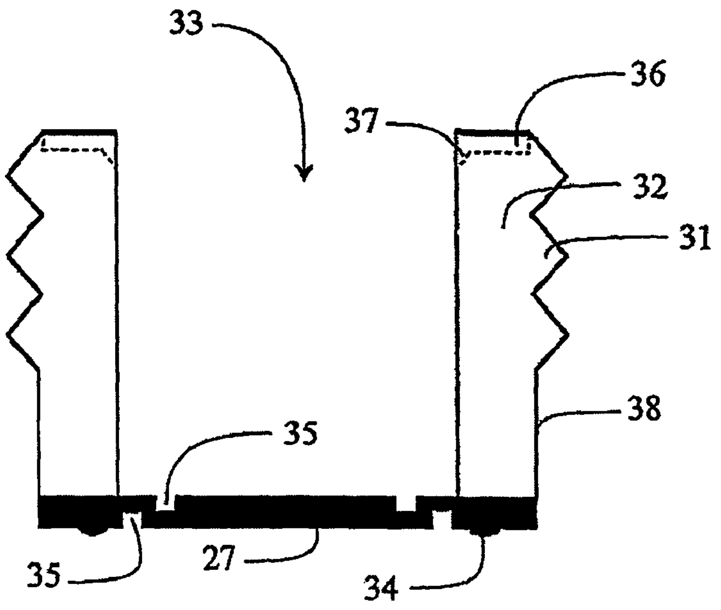

FIG. 3A illustrates a cross-section of a first embodiment of an implantable device 1 according to the invention. The device is preferably substantially cylindrically shaped and provided with a screw thread 31 on upstanding walls of the frame 32. Inside the frame is a cavity 33, provided for receiving a stimulating and/or sensing member, as will be described hereinafter. The device preferably has a height of 2 to 4 mm and a diameter of approximately 0.6 to 2 mm. The frame 32 is made of bio-compatible material such as for example titanium. The advantage of using titanium is that this material oxides at its surface, thus enabling osseointegration—a strong direct connection with the bone tissue.

A bottom wall part of the frame is formed by a membrane 27, which is preferably manufactured of a thin (a few im) biocompatible metallic sheet, such as for example titanium, laser-welded 34 at the edges of the frame. In order to decrease the mechanical impedance of the membrane a few circular corrugations 35 can be made on its surface (on one or both sides) forming a kind of hinge increasing the flexibility of the membrane. The membrane 27 and the rest of the frame together form an interface with the inner ear 12. The interface is provided for energy transfer from and towards the inner ear 12.

The size/diameter of the flexible metallic membrane 27 in the proposed embodiment is approximately 0.8 mm, but it may be larger but also much smaller, even e.g. 0.4 mm (in stapes surgery even the pistons with the diameter of 0.4 mm allow for full restoration of hearing). The edges of the frame and are preferably smoothed in order to avoid injury when implanting the device.

The membrane 27 is coupled to the frame 32 and electrically dissociated or insulated from an electrical signal output circuitry of the vibration actuator to be applied into the device 1. The frame 32 of the device is further provided with slots 36 applied on an upper peripheral of the frame as illustrated in FIG. 4. The slots are further preferably provided with inclined cut-outs 37 extending towards the inner side of the frame. The slots are provided for anchoring a mounting tool (not shown in the drawings) enabling to mount the device in the inner ear. The inclined cut-outs enable to provide protrusions on the mounting tool which are provided to fit into the cut-outs, thus enabling a better anchoring of the mounting tool into the slots.

This embodiment is provided for implantation by pushing the device 1 into a precisely calibrated opening 29 in the inner ear wall 25. For this purpose the lower part of the frame has cylindrical walls 38 without a screw thread. It can, however, be roughened in order to improve fixation In the bony wall 25 of the inner ear.

Figure 3B:
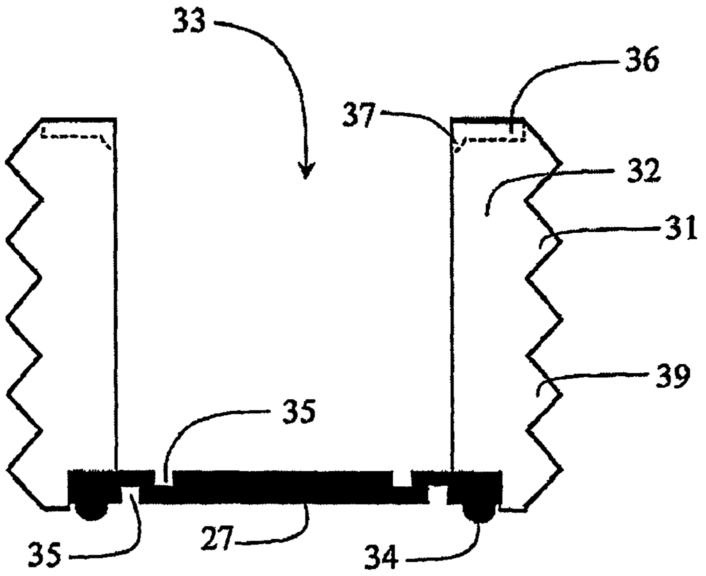

The embodiment illustrated in FIG. 3B distinguishes from the one illustrated in FIG. 3A by a screw thread 39 on the bottom part of the frame 32. This embodiment is provided for implantation by screwing the device into a pre-tapped opening 28 in the inner ear bony wall. While screwing the device into the bony wall preferably a predetermined torque is applied. This torque is realized by an insertion device (not depicted in the figures).

Figure 3C:
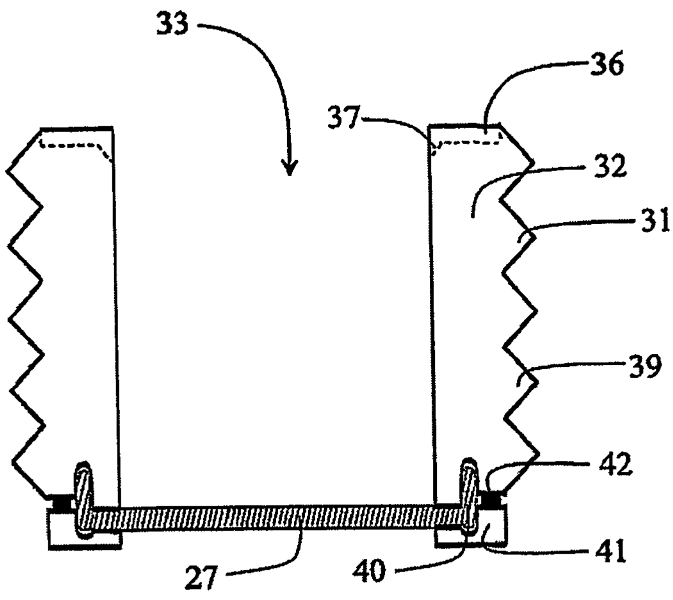

The embodiment illustrated in FIG. 3C distinguishes from the one illustrated in FIG. 3A by a different type of the membrane 27 applied to the frame. This membrane is made of a biocompatible flexible material, preferably silicone, and has a thicker ring 40 at its perimeter allowing for fixation of the membrane 27 to the frame 32. The membrane 27 is manufactured e.g. by spinning a silicone droplet using a spinning machine and connecting the thus obtained membrane with an external silicone ring 40 before full polymerisation is obtained. A further ring 41 could be applied on the frame in order to fix the membrane 27. The further ring 41 is either welded 42, for example by laser welding, or screwed to the frame 32. The edges of the frame 32 and the further ring 41 are preferably smoothed in order to avoid injury when implanting the device 1.

Figure 3D:
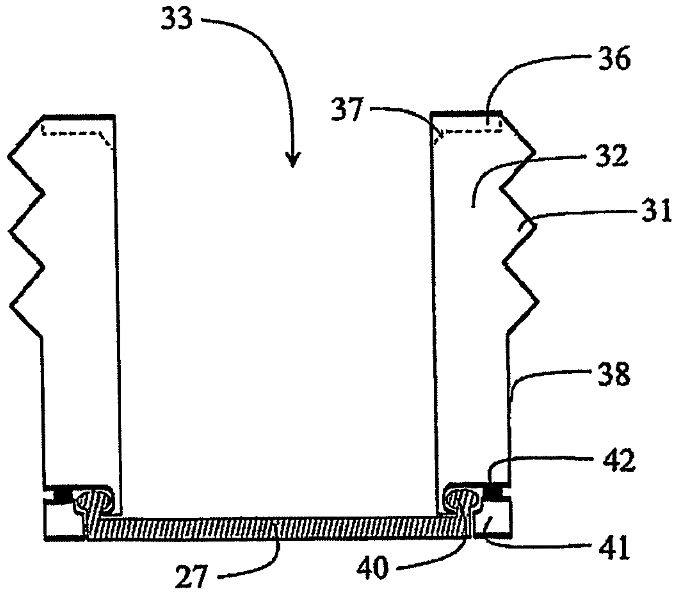

FIG. 3D shows another variant of fixation of the flexible membrane 27 to the frame 32 relative to the embodiment depicted in FIG. 3C. The silicone ring 40 of the membrane 27 is only applied on the upper part of the perimeter of the membrane 27, in such a manner, that after application on the frame 32 and welding 42 the further ring 41, the membrane 27 and the further ring 41 are flush with the bottom part of the frame 32.

Figure 3E:
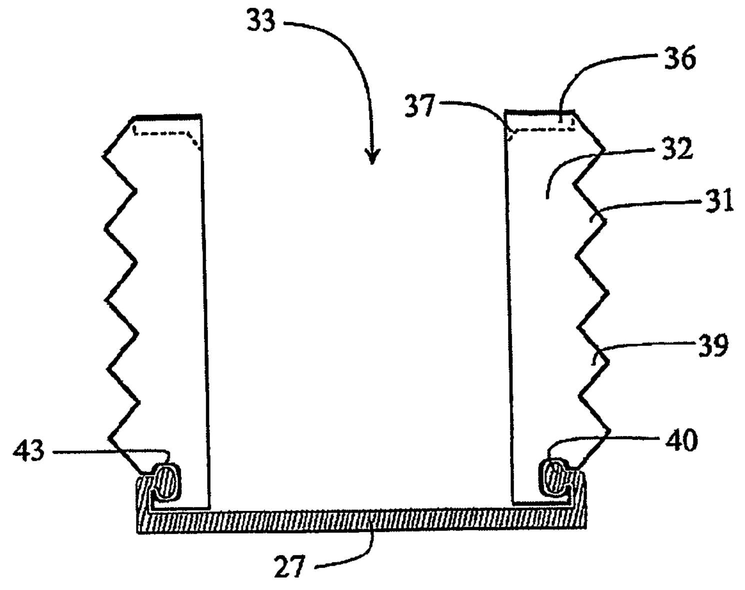

The embodiment illustrated in FIG. 3E comprises a membrane 27 having a C-shaped border and wherein the silicone ring 40 is applied on the upper side of the C-shaped border. The frame comprises an annular groove 43 applied on the external wall of the frame for accommodating the silicone ring 40. Also this embodiment enables a flush mounting of the membrane 27 on the underside of the frame 32.

Figure 3F:
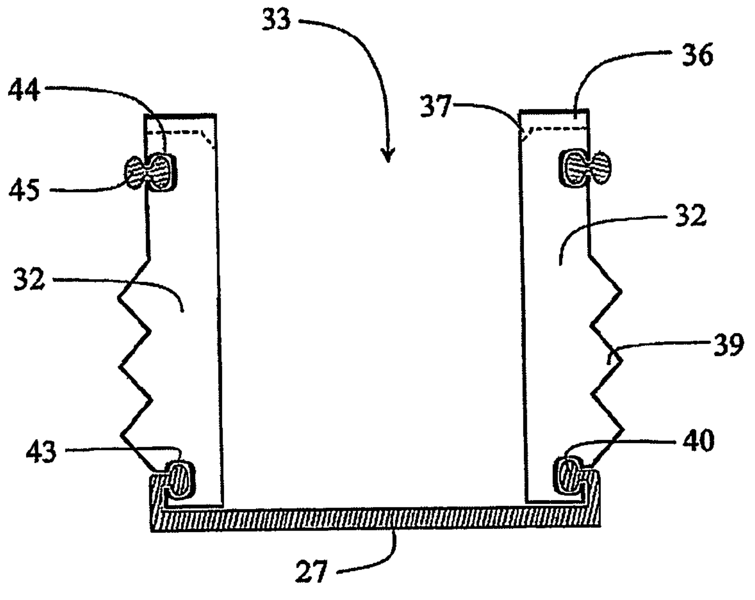

The embodiment illustrated in FIG. 3F is analogous to the one shown in FIG. 3E but distinguishes by the presence of a further external annular groove 44 applied on an upper side of the external frame wall. An O-ring 45 is housed in the further groove 44 enabling to fix a stimulating/sensing member thereon.

In all the embodiments the membrane 27 is provided to form a substantially hermetical closure between the perilymph 18, facing the outer side of the membrane 27 and an inner part 33 of the frame 32, with which the other side of the membrane 27 is in contact. This hermetical closure provides an adequate protection of the perilymph fluid 18 and avoids contamination.

Figure 4A:
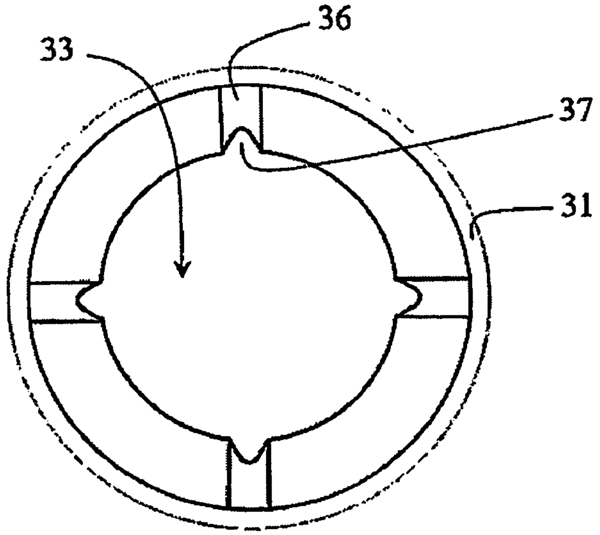
Figure 4B:
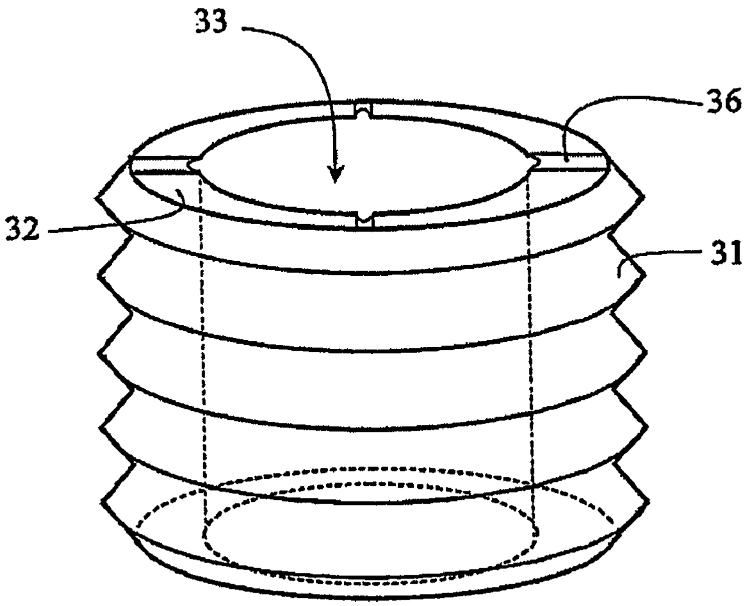
Figure 4C:
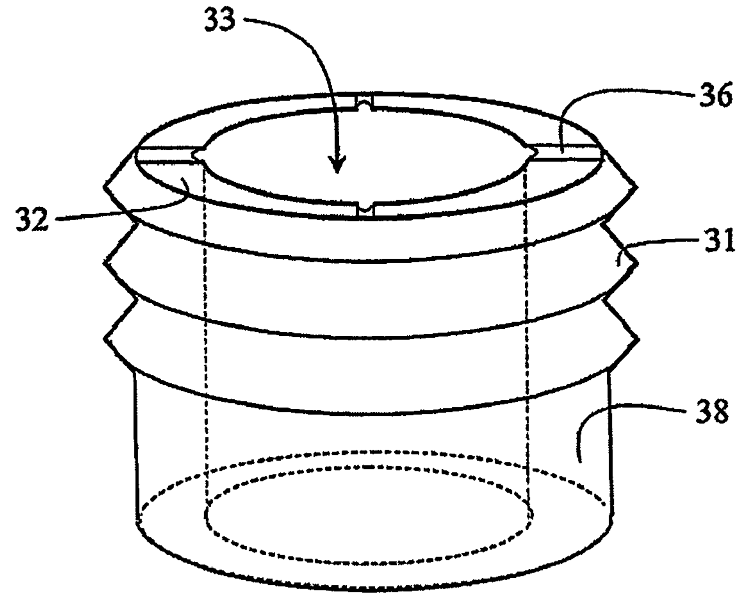
Figure 4D:
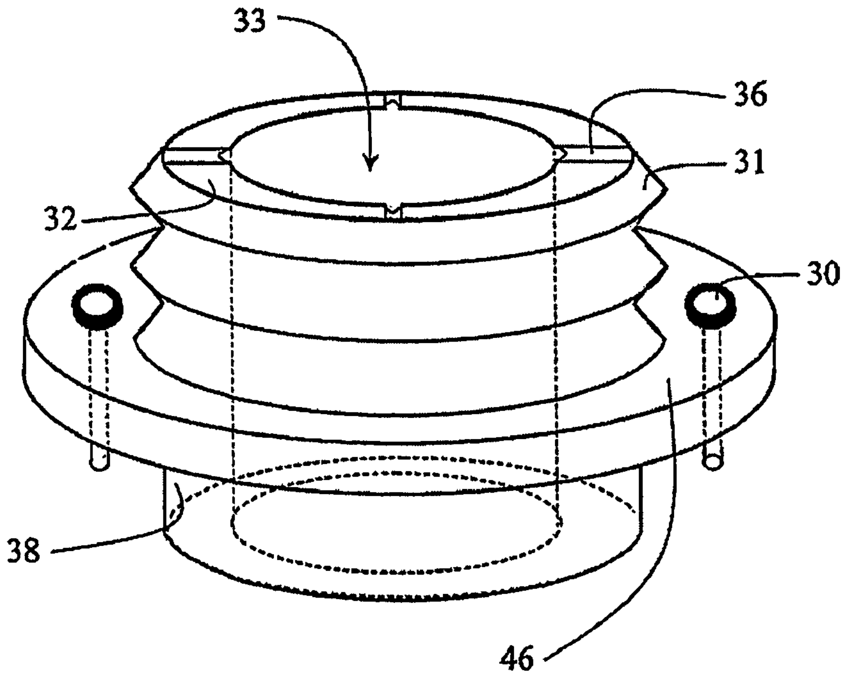

FIG. 4A shows a top view and FIG. 4B to D show side views of the preferred embodiments. The embodiment shown in FIG. 4B is provided for implantation by screwing into the bony wall 25 of the inner ear 12. The embodiment shown in FIG. 4C is provided for implantation by pushing into precisely calibrated opening 29 in the bony wall 25 of the inner ear 12. The embodiment shown in FIG. 4D is analogous to the embodiment depicted in FIG. 4C, but is provided with a collar 46 allowing for additional fixation of the device to the bony wall 25 of the inner ear 12 by means of micro-screws 30.

FIG. 5 A shows a cross-section of a further embodiment of a device 1 as component of a combined set according to the invention. This embodiment secures conductive coupling between the middle 7 and inner ear 12 spaces and allows for sensing of various electrical potentials generated acoustically, electrically or by any other type of triggering signal. The sensed signals, such as the compound action potentials (CAP), cochlear microphonic (CM), etc. can be used for diagnostic purposes as well as for feed-back regulation of the sensing/stimulating devices connected to the disclosed device 1. In this embodiment the membrane 27 is provided on its outer side, i.e. the side facing the perilymph 18, with an electrically conductive layer 47, which is connected to a conductive wire 48, applied in an electrically isolated manner on the frame 32. The isolation of the electrical connection of the wire 48 at the top of the frame 32 is realised by means of a glass feed-through 49. Care is taken that the wire crosses the membrane 27 in a fluid light manner. The conductive layer 47 is also made of a bio-compatible metal, for example platinum or gold, and is formed by a circular sheet fixed to the outer surface of the membrane 27. Alternatively the conductive layer could be obtained by direct metallization of the silicone membrane 27. The metallic frame is also conductive and forms a second electrode connected to a further wire 50.

The membrane 27 is electrically insulated from an electrical signal, produced by a sensing and/or stimulating device, as will be described in more detail hereinafter. The application of the conductive layer 47 enables to apply or sense electric signals directly to/from the perilymph 18, without affecting the isolating function of the membrane 27.

Figure 5A:
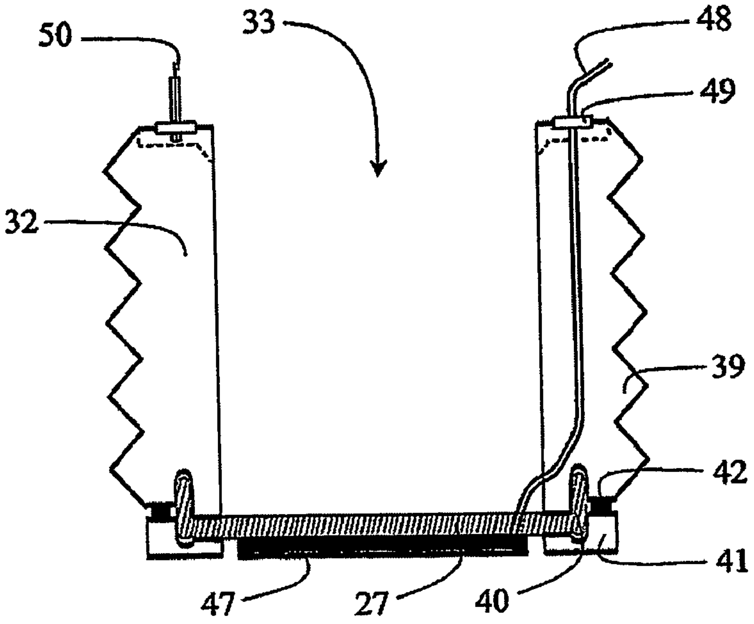
Figure 5B:
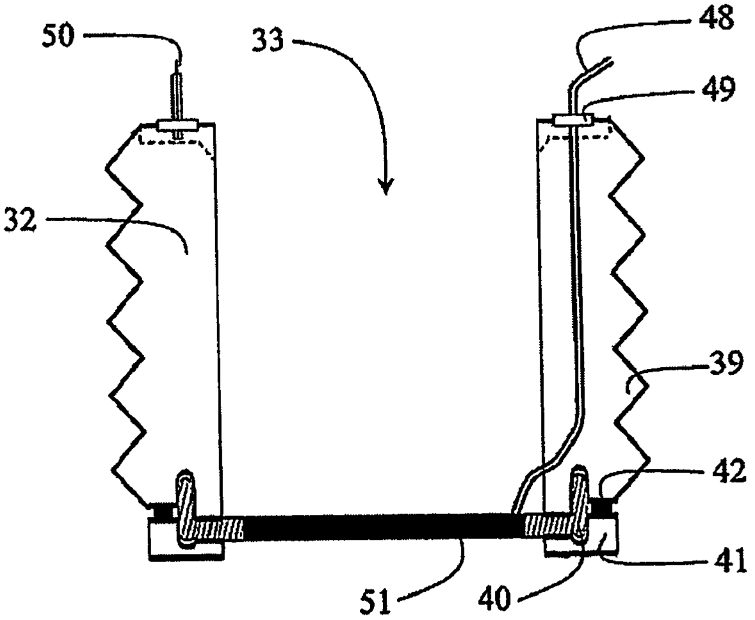

The embodiment illustrated in FIG. 5B distinguishes from the one illustrated in FIG. 5A by the fact that the conductive metallic element 51 is incorporated in the central part of the silicone membrane 27.

Figure 5C:
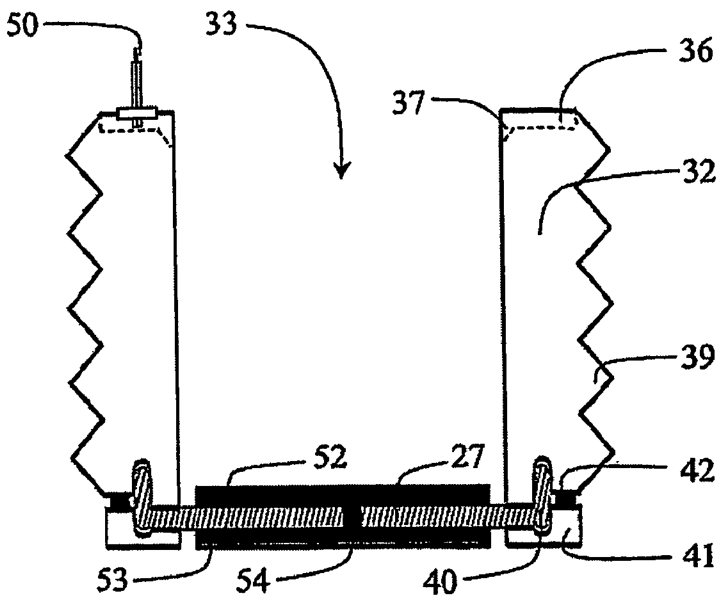

In the embodiment illustrated in FIG. 5C both sides of the membrane 27 are provided with a conductive layer 52 and 53 connected to each other by a connecting member 54 extending through the membrane 27. Both layers and the connecting member are made of bio-compatible metal, for example platinum. The layers are preferably circularly shaped. They are fixed to the membrane by means of the connecting member 54 or obtained by direct metallization of the membrane27. The inner conductive layer 52 serves for electrical connection with a sensing and/or stimulating device.

Figure 5D:
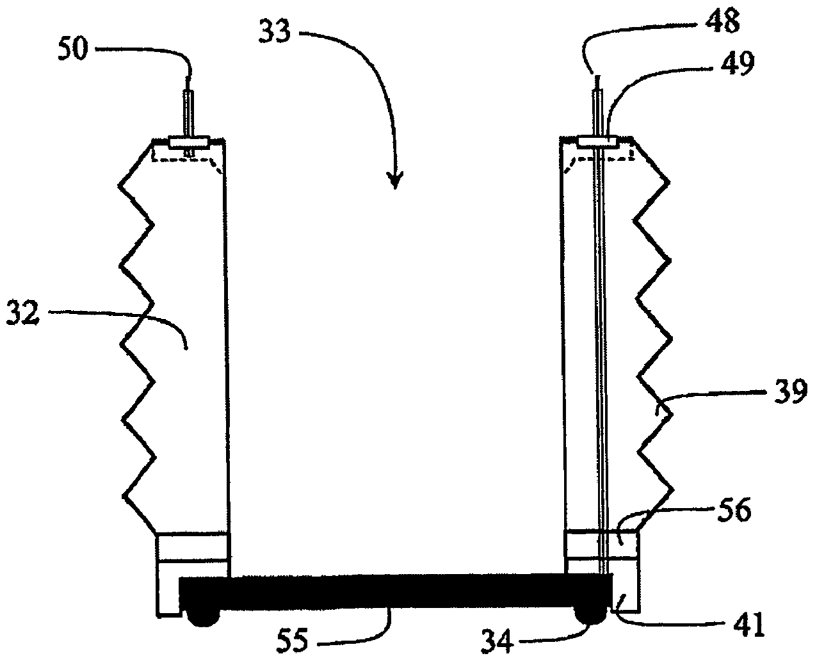

FIG. 5D shows an embodiment where the whole flexible membrane is made of conductive metal 55 and is laser-welded 34 at the perimeter to the frame 32. The conductive membrane 55 and the further ring 41 are insulated from the rest of the frame 32 with as insulating ring 56. The conductive membrane 55 is connected to a conductive wire 48, applied in an electrically isolated manner on the frame 32.

The implantable device as component of the combined set, functions as a stand-alone device to be used as an interface with the inner ear suitable for treatment and diagnosis of a wide range of otological pathologies. In particular it is suitable to be used as an interface for coupling of the physiological vibrations of the ossicular chain to the inner ear. The advantage of the proposed device is that it provides an interface with the inner ear, which is flexible yet rugged enough to withstand differences in the ambient pressure allowing for columellar type of prosthetic reconstruction of the ossicular chain. In cases of otosclerosis, where with standard techniques a perforation is made in the frequently difficultly accessible stapes footplate, coupling of the ossicular chain to the device's membrane (and not directly to the cochlear fluid space) could substantially facilitate the surgery and decrease the number of complications. Interposition of prosthesis between the ossicular chain and the disclosed device would additionally decrease the chances for prosthesis migration by stabilization of the distal end of the prosthesis in the opening of the device's frame. In chronic middle ear pathology with or without cholesteatoma the disclosed device could offer the safe yet effective solution for restoration of functional hearing. This is a very important application, since in patients with chronic middle ear pathology and frequent concomitant fixation of the stapes, there exist currently no safe surgical procedures that can improve hearing. In such cases a permanent opening of the inner ear space e.g. in order to place a piston in this opening, can lead to infection of the inner ear and cophosis.

The implantable device as component of a combined set is also provided to be used in connection with other stimulating and/or sensing appliances suitable for diagnosis and treatment of hearing loss, tinnitus, vertigo and/or pain. For instance it can become a part of a device sensing the movements or the pressures inside the inner ear for a wide range of frequencies, from DC to ultrasound. This feature can be employed in various types of microphones as well as in diagnostic and treatment applications. An example of such application is the Ménière's disease, where the implantable device, as component of a combined set, can be used for coupling of a diagnostic/treatment tool provided for measuring the pressures and potentials generated in the inner ear and/or generating e.g. pressure pulses.

In cases of oval and/or round window aplasia it can aid to restore the mechanics of the inner ear. In such cases placement of one or two disclosed devices could restore the physiological pressure relations between the scala vestibuli and the scala tympani and help improve hearing.

Figure 6:
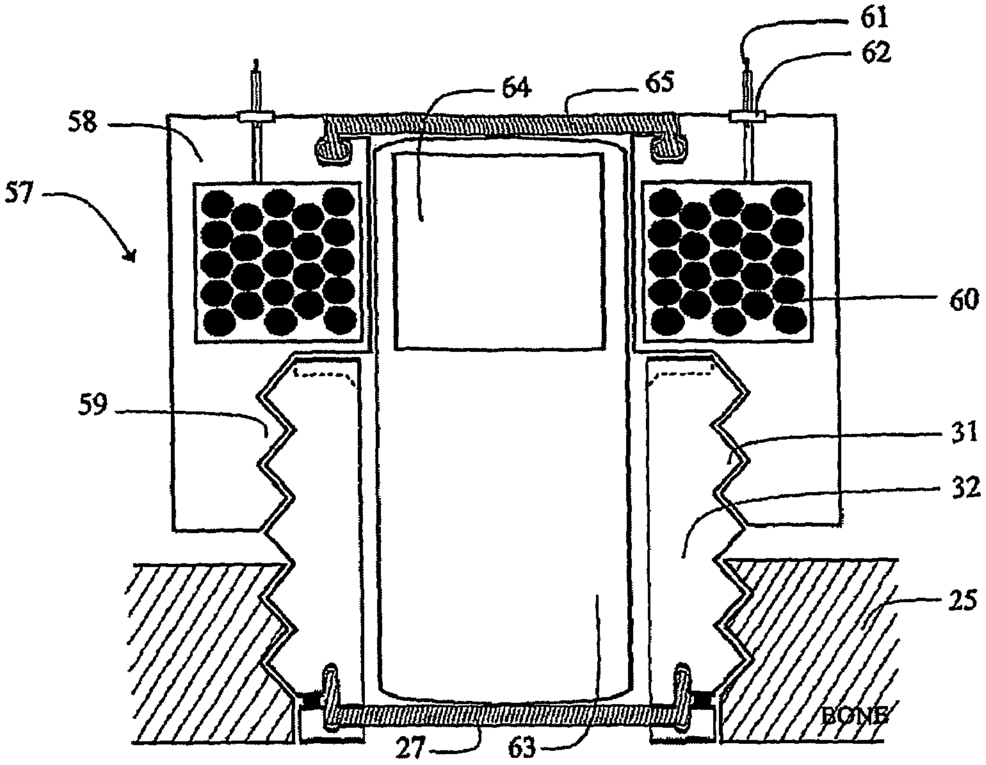
FIG. 6 shows the cross-section of the combined set provided with an electromagnetic stimulating/sensing device.

FIG. 6 illustrates in cross-section an example of the combined set according to the present invention and provided with an electromagnetic sensing and/or stimulating member 57. In order to connect the latter member to the device 1, connecting means are applied on the frame 32. In the example illustrated in FIG. 6, the connecting means are formed by extending the frame 32 of the device 1 in such a manner, that the external screw thread 31 extends above the bony wall 25 of the inner ear 12, when the device is applied in the inner ear. The sensing and/or stimulating member 57 is lodged in a housing 58 provided with an internal screw thread 59, matching with the screw thread 31 of the device, in such a manner as to screw the housing 58 onto the frame 32.

A coil 60 is placed inside the housing 58 and connected to insulated wires 61 carrying a stimulating electrical current to be fed to the coil 60. The wires 61 are insulated from the housing 58 for example by leading them through a glass feed-through 62 in the housing 58. The stimulating current applied on the coil 60 causes a varying magnetic field to be created by the coil 60, causing on its turn the vibration of a piston 63 contained partially inside the lumen of the coil.

The piston 63 could also be used as a sensing member. Movement of the piston 63 will then cause AC currents to be induced into the coil 60. Those currents can then be picked up by the wires 61 and be led to an analyser. The membrane is in this configuration used to transfer energy from the inner ear 12 to the vibration actuator 57. The piston is preferably made of Teflon (registered trademark) and comprises a micromagnet 64 in its upper part. The upper surface of the piston is fixed to a flexible membrane 65, for example made of silicone, closing the central part of the housing 58. The other end of the piston 63 contacts the flexible membrane 27. Both ends of the piston 63 are preferably rounded to ensure a better contact with the respective membranes. The movement of the piston will then drive the membrane 27 in order to transfer energy to the inner ear 12.

The membrane 65 serves two purposes, first the one to provide a flexible suspension to the piston 63 allowing it to vibrate and to transfer in such a manner vibratory energy to the membrane 27, and secondly, if the elasticity of membranes 65 and 27 matches, then this can be used for adjusting the pre-loading force exerted by the piston 63 on the membrane 27 when mounting the member 57. Observed increased bulging of the membrane 65 would correspond to the bulging of the membrane 27. When a membrane 27 with an electrical conductive layer such as illustrated in FIGS. 5B to 5D is used, another way to monitor a good contact between the piston 63 and the membrane 27 is the measurement of the electrical resistance between the conductive layer on the membrane 27 and the piston 63. In this case, the piston 63 should be provided with an additional conductive contact on its bottom part (not depicted in the figure).

The membrane 27 is electrically insulated from the electrical signal applied on the coil 60 as there is only a mechanical contact between the membrane 27 and the piston 63. The membrane 27 thus serves as an interface between the piston 63 and the perilymph 18 and enables to transfer energy from and/to the perilymph 18 to the member 57, without electrical contact between the membrane 27 and the electrical output circuitry of the member 57.

Figure 7:
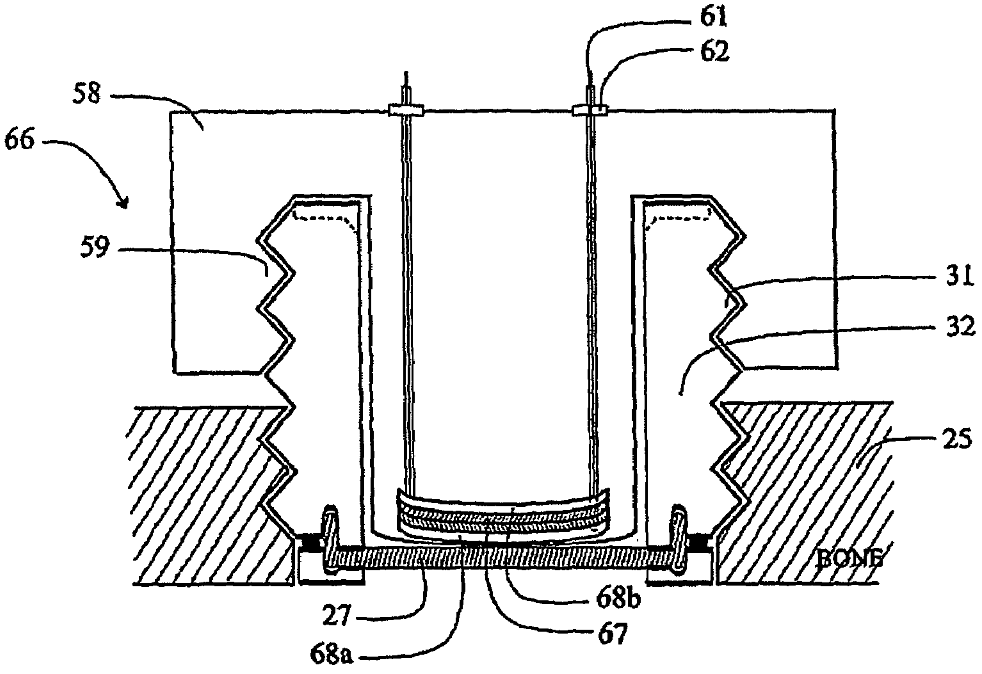
FIG. 7 shows the cross-section of the combined set provided with a piezo-electric stimulating/sensing device.

FIG. 7 illustrates in cross-section the device according to the present invention and provided with a piezo-electric sensing and/or stimulating member 66. The latter member is applied in a similar manner as the electromagnetic embodiment illustrated in FIG. 6. The housing 58 lodges a piezo-electric transducer 67 housed in a bottom part. Electrical insulated wires 62 are provided to supply an electrical stimulating current to the piezo-electric transducer 67. The latter is mounted between two bio-compatible electrodes 68*a* and *b*. The piezo-electric transducer 67 is for example made of stress-biassed lead lanthanum zirconia titanate (PLZT). A stimulating AC voltage supplied to the electrodes 68*a* and *b* causes the piezo-electric transducer to vibrate, which vibrations are mechanically supplied to the membrane 7, since the piezo-electric transducer 67 contacts mechanically the membrane 27. When used as a sensing member, the forces exerted on the piezo-electric transducer 67 by the vibration of the membrane 27 will induce voltage at the sides of the piezo-electric transducer 67. The latter is preferably rounded to ensure a better contact with the membrane 27. The pre-loading forces are controlled in an analogous manner as described with the electromagnetic embodiment. Also in this embodiment there is an electrical dissociation between the membrane 27 and the electrical output circuitry of the member 66.

Figure 8:
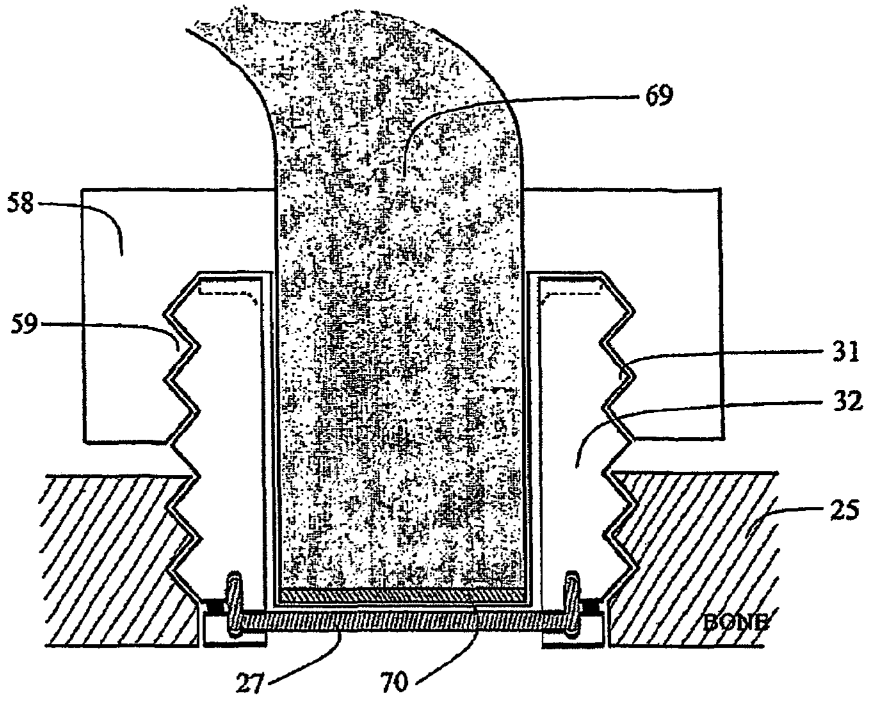
FIG. 8 shows the cross-section of the combined set provided with a fluid filled conduct serving for energy transmission from a remote transducer.

FIG. 8 shows an embodiment of the device according to the present invention in combination with a remote sensing and/ or stimulating member. The coupling between the remote member and the membrane 27 is realised by means of a tube 69 filled with a fluid such as for example liquid silicone. The tube is connected to one side with a remote transducer (not shown) and on the other side inserted into the frame 32 of the device 1 in order to mechanically contact the membrane 27. The tube 69 is hermetically closed with a further membrane 70 juxtaposed to membrane 27. The tube is mounted in a housing 58 as previously described. The remote transducer is for example a piezo-electric or electromagnetic transducer but could also be a pressure generator.

Figure 9:
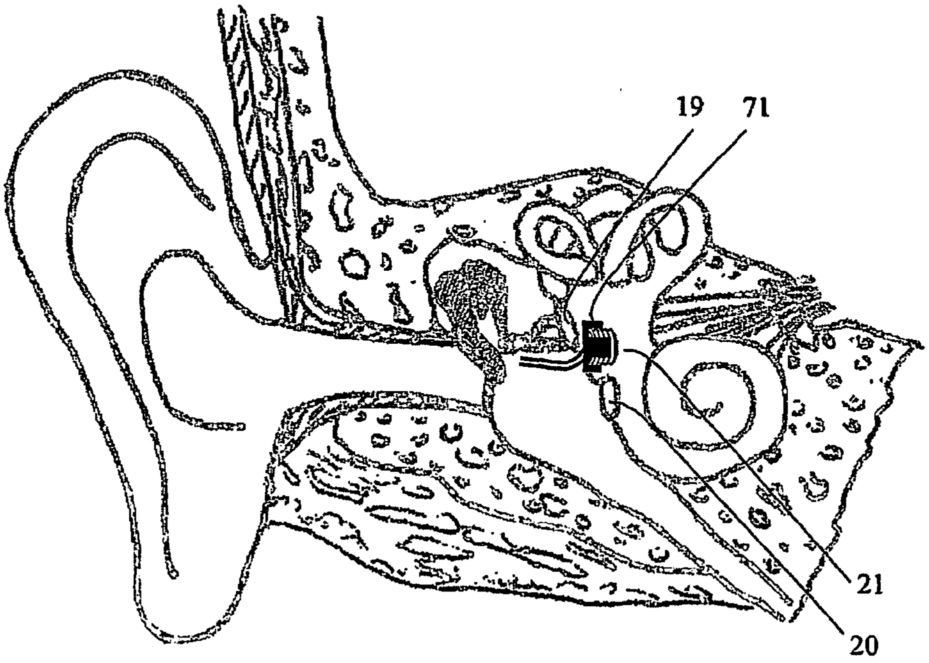
FIG. 9 shows how the combined set is implanted in the wall of the inner ear.

FIG. 9 shows how the combined set 71 comprising the implantable window and the vibration actuator is implanted in the bony wall 25 of the inner ear 12.

Figure 10A:
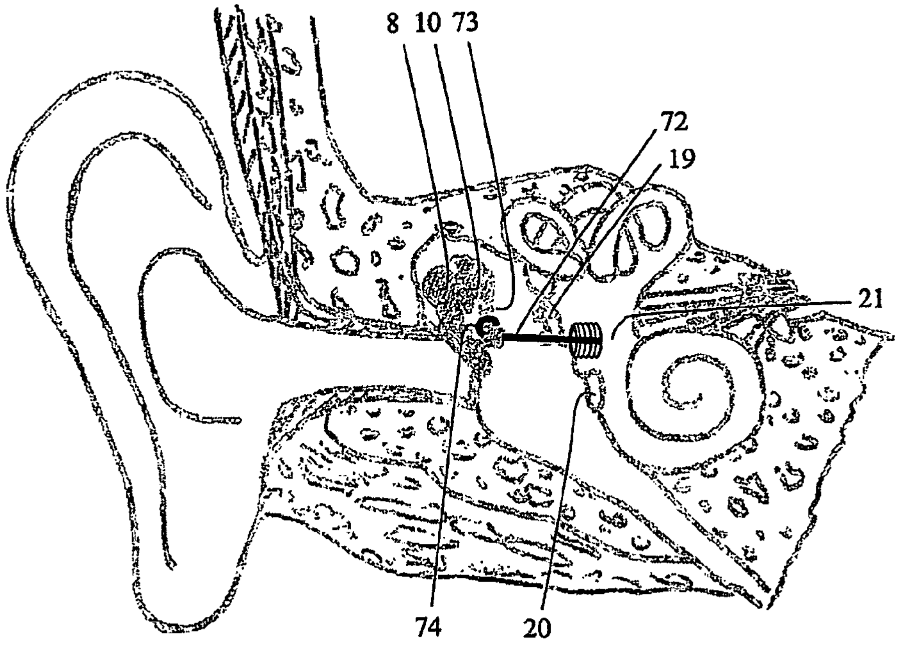
FIGS. 10A and B show the device provided with a connection with the ossicular chain.

FIG. 10A shows an exemplary coupling of the ossicular chain to the device 1 as component of a combined set according to the invention. This type of connection can be used e.g. in the cases of otosclerosis, where the footplate of the stapes is fixed in the oval window 19, which results in immobility of the ossicular chain. In these cases, after removal of the stapes superstructure (i.e. the head an the crura), the ossicular chain becomes mobile again. Then prosthesis 72 can be placed between the long process 73 of the incus 10 and the membrane 27. The fragment 74 of the prosthesis connecting to the incus may be curved in such a way that it embraces the long process 73 of the incus 10 and may be closed on it by squeezing with micro-forceps. Such an approach allows avoid opening of the stapes footplate 19 and creation of a permanent opening between the middle ear 7 and the perilymphatic space 18 of the inner ear 12. Also the connection of the prosthesis 72 with the membrane 27 is easier due to a better access as well as more stable, since the construction of the device prevents migration of the distal end of the prosthesis 72.

Figure 10B:
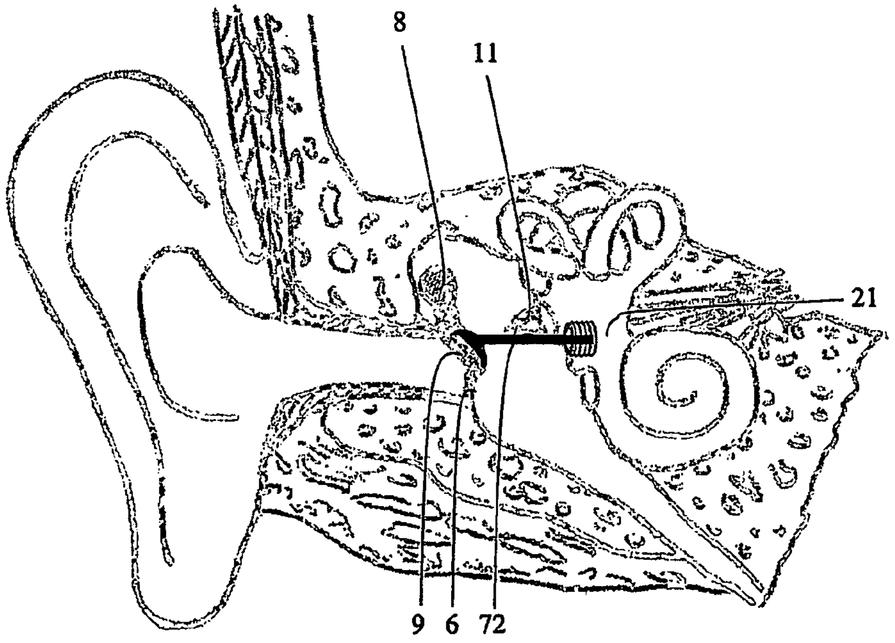

FIG. 10B shows another exemplary coupling of the ossicular chain to the device 1 as component of a combined set according to the invention. This type of connection can be used for otosclerosis too, however it is also suitable for functional reconstructions in chronic middle ear pathologies with or without cholesteatoma. In these cases the ossicular chain is frequently disrupted and the remnants of it must be removed. Also in many cases the stapes footplate in the oval window 19 is difficult to identify or it may be fixed. Therefore, in such cases, the prosthetic coupling 72 may be realised between the membrane 27 of the device 1 and the remnants of the shaft 9 of the hammer 8 or between the device and the native or grafted tympanic membrane 6. In the cases of chronic middle ear pathology performing a permanent opening penetrating from the middle ear 7 to the fluid space 18 of the inner ear 12 is very dangerous and might in many cases result in infection of the inner ear 12 followed by fatal meningitis or total deafness. Therefore the concept of the device according to the invention, which creates an interface for transfer of mechanical energy, yet still separates the middle 7 and the inner ear 12 with the membrane 27 offers a very attractive solution for these cases.

The combined set, according to the present invention, is mainly used in the treatment of hearing loss due to chronic middle ear disease, otosclerosis and other ear pathologies resulting in compromised hearing. Direct interface with the inner ear tissues allows to obtain substantial acoustic effects with only minimal force. Yet the fact that the vibration actuator is isolated from the inner ear fluid spaces practically precludes possible complications. Another major advantage of the proposed device is that it does not interfere with the normal anatomy and function of the human hearing organ and therefore implantation of which should not by itself cause or induce hearing loss. The disclosed device does not connect to the middle ear ossicles, therefore it can also be used in different chronic middle ear pathologies, where the ossicular chain is damaged or its mobility is compromised. No link with the ossicular chain results also in an additional advantage—vibrators coupled to the disclosed device do not suffer from the high frequency filtering inherent to the physiological transfer function of the middle ear ossicles.

The invention claimed is:

1. A combined set comprising a vibration actuator and an implantable device to be used as an artificial fenestra implantable in a bony wall of an inner ear, said device comprising a frame made of a bio-compatible material and provided to be applied at least partially in said bony wall, said frame being provided with a wall part formed by a membrane made of a bio-compatible material and forming a barrier with a perilymph of said inner ear when applied in said bony wall, said membrane being provided to form together with said frame an interface with said inner ear, said interface being provided for energy transfer, in particular mechanical and/or electrical and/or electromagnetic energy, towards said inner ear, said vibration actuator being provided for generating a vibration energy, characterized in that said membrane is electrically dissociated from said vibration actuator and provided for receiving said vibration energy from said vibration actuator, said membrane being further provided for transferring energy from said inner ear, characterized in that said device is provided with connecting means applied on said frame, said connecting means being provided for connecting said vibration actuator and/or a sensing member into said frame in such a manner as to enable said energy transfer.

2. A combined set as claimed in claim 1, characterized in that said vibration actuator comprises an electrical signal output circuitry provided for output of said vibration energy, said membrane being electrically dissociated from said circuitry.

3. A combined set as claimed in claim 1, characterized in that said vibration actuator is formed by an electromagnetic stimulating and/or sensing member mounted into said frame, said member comprising an electromagnetically driven actuator mechanically contacting said membrane within said frame.

4. A combined set as claimed in claim 1, characterized in that said vibration actuator is formed by a piezo-electric stimulating and/or sensing member mounted into said frame, said member comprising a piezo-electrically driven actuator mechanically contacting said membrane within said frame.

5. A combined set comprising a vibration actuator and an implantable device to be used as an artificial fenestra implantable in a bony wall of an inner ear, said device comprising a frame made of a bio-compatible material and provided to be applied at least partially in said bony wall, said frame being provided with a wall part formed by a membrane made of a bio-compatible material and forming a barrier with a perilymph of said inner ear when applied in said bony wall, said membrane being provided to form together with said frame an interface with said inner ear, said interface being provided for energy transfer, in particular mechanical and/or electrical and/or electromagnetic energy, towards said inner ear, said vibration actuator being provided for generating a vibration energy, characterized in that said membrane is electrically dissociated from said vibration actuator and provided for receiving said vibration energy from said vibration actuator, said membrane being further provided for transferring energy from said inner ear, characterized in that said vibration actuator is formed by a mechanically driven piston mounted into said frame, said piston being provided for generating vibrations and being mounted in such a manner as to mechanically contact said membrane.

6. A combined set as claimed in claim 5, characterized in that said vibration actuator comprises an electrical signal output circuitry provided for output of said vibration energy, said membrane being electrically dissociated from said circuitry.

7. A combined set as claimed in claim 5, characterized in that said vibration actuator is formed by an electromagnetic stimulating and/or sensing member mounted into said frame, said member comprising an electromagnetically driven actuator mechanically contacting said membrane within said frame.

8. A combined set as claimed in claim 5, characterized in that said vibration actuator is formed by a piezo-electric stimulating and/or sensing member mounted into said frame, said member comprising a piezo-electrically driven actuator mechanically contacting said membrane within said frame.

9. A combined set comprising a vibration actuator and an implantable device to be used as an artificial fenestra implantable in a bony wall of an inner ear, said device comprising a frame made of a bio-compatible material and provided to be applied at least partially in said bony wall, said frame being provided with a wall part formed by a membrane made of a bio-compatible material and forming a barrier with a perilymph of said inner ear when applied in said bony wall, said membrane being provided to form together with said frame an interface with said inner ear, said interface being provided for energy transfer, in particular mechanical and/or electrical and/or electromagnetic energy, towards said inner ear, said vibration actuator being provided for generating a vibration energy, characterized in that said membrane is electrically dissociated from said vibration actuator and provided for receiving said vibration energy from said vibration actuator, said membrane being further provided for transferring energy from said inner ear, characterized in that said vibration actuator is formed by a pressure generator mounted into said frame, said pressure generator being provided for driving said membrane.

10. A combined set as claimed in claim 9, characterized in that said vibration actuator comprises an electrical signal output circuitry provided for output of said vibration energy, said membrane being electrically dissociated from said circuitry.

11. A combined set as claimed in claim 9, characterized in that said vibration actuator is formed by an electromagnetic stimulating and/or sensing member mounted into said frame, said member comprising an electromagnetically driven actuator mechanically contacting said membrane within said frame.

12. A combined set as claimed in claim 9, characterized in that said vibration actuator is formed by a piezo-electric stimulating and/or sensing member mounted into said frame, said member comprising a piezo-electrically driven actuator mechanically contacting said membrane within said frame.

13. An implantable device for use as an artificial fenestra implantable in a bony wall of an inner ear, the implantable device comprising a bio-compatible frame and provided to be applied at least partially in the bony wall, the frame including a wall part formed by a bio-compatible membrane and forming a barrier with the inner ear perilymph when the frame is applied in the bony wall, the membrane being provided to form together with the frame an interface with the inner ear, the interface being provided for transferring energy, in particular mechanical and/or electrical and/or electromagnetic energy, towards the inner ear, the membrane being provided for receiving vibration energy from a vibration actuator, the membrane being electrically dissociated from the vibration actuator, and the membrane being provided for transferring energy from the inner ear when the device is mounted in the inner ear, characterized in that said frame is coated with antibiotics and/or a substance promoting bone tissue growth.

14. An implantable device as claimed in claim 13, characterized in that a side of said membrane, provided to contact said perilymph when said device is mounted in said inner ear, is provided with electrically conductive means which are connected to a conductive wire applied in an electrically insulated manner on said frame.

15. An implantable device as claimed in claim 13, characterized in that a side of said membrane, provided to contact said perilymph when said device is mounted in said inner ear, is provided with electrically conductive means which are connected to said frame.

16. An implantable device as claimed in claim 13, characterized in that said frame is dimensioned in such a manner as to insert at least partially said vibration actuator and/or sensing member therein.

17. An implantable device as claimed in claim 13, characterized in that said device is substantially cylindrically shaped and provided with a screw thread on upstanding walls.

18. An implantable device as claimed in claim 13, characterized in that said membrane is provided to form a substantially hermetical closure between said perilymph and an inner part of said frame when applied in said inner ear.

19. An implantable device as claimed in claim 13, characterized in that said membrane is made of titanium.

20. An implantable device for use as an artificial fenestra implantable in a bony wall of an inner ear, the implantable device comprising a bio-compatible frame and provided to be applied at least partially in the bony wall, the frame including a wall part formed by a bio-compatible membrane and forming a barrier with the inner ear perilymph when the frame is applied in the bony wall, the membrane being provided to form together with the frame an interface with the inner ear, the interface being provided for transferring energy, in particular mechanical and/or electrical and/or electromagnetic energy, towards the inner ear, the membrane being provided for receiving vibration energy from a vibration actuator, the membrane being electrically dissociated from the vibration actuator, and the membrane being provided for transferring energy from the inner ear when the device is mounted in the inner ear, characterized in that said frame is coated with antibiotics and/or a substance promoting bone tissue growth, characterized in that said frame is coated with a substance improving hermeticity of insertion into said perilymph.

21. An implantable device as claimed in claim 20, characterized in that a side of said membrane, provided to contact said perilymph when said device is mounted in said inner ear, is provided with electrically conductive means which are connected to a conductive wire applied in an electrically insulated manner on said frame.

22. An implantable device as claimed in claim 20, characterized in that a side of said membrane, provided to contact said perilymph when said device is mounted in said inner ear, is provided with electrically conductive means which are connected to said frame.

23. An implantable device as claimed in claim 20, characterized in that said frame is dimensioned in such a manner as to insert at least partially said vibration actuator and/or sensing member therein.

24. An implantable device as claimed in claim 20, characterized in that said device is substantially cylindrically shaped and provided with a screw thread on upstanding walls.

25. An implantable device as claimed in claim 20, characterized in that said membrane is provided to form a substantially hermetical closure between said perilymph and an inner part of said frame when applied in said inner ear.

26. An implantable device as claimed in claim 20, characterized in that said membrane is made of titanium.

* * * * *